US005290925A

United States Patent [19]
Fino

[11] Patent Number: 5,290,925
[45] Date of Patent: Mar. 1, 1994

[54] METHODS, KITS, AND REACTIVE SUPPORTS FOR 3' LABELING OF OLIGONUCLEOTIDES

[75] Inventor: James R. Fino, Antioch, Ill.

[73] Assignee: Abbott Laboratories, Abbott Park, Ill.

[21] Appl. No.: 630,908

[22] Filed: Dec. 20, 1990

[51] Int. Cl.$^5$ .................. C12Q 1/68; C03C 12/00; C07H 17/00
[52] U.S. Cl. .................. 536/25.32; 501/33; 524/1; 435/6
[58] Field of Search .............. 435/6; 536/27, 25.3, 536/25.32; 568/700, 840; 548/303; 501/33; 524/1

[56] References Cited

FOREIGN PATENT DOCUMENTS 330221 8/1989 European Pat. Off. ....... C12Q 1/68

OTHER PUBLICATIONS

Humphrey et al. (1970), Immunology for Students of Medicine, 3rd edition, (Blackwell Scientific Publications, Oxford), p. 715.
Goodchild, Bioconjugate Chemistry, 1(3):165-187 (1990).
Kempe, et al, Nucleic Acids Research, 13(1):45-57 (1985).
Zuckermann, et al., Nucleic Acids Research, 15(13):5305-5321 (1987).
Nelson, et al., Nucleic Acids Research, 17(18):7187-7194 (1989).
Usman, et al., Tetrahedron Letters, 29(38):4831-4834 (1988).

Primary Examiner—Richard A. Schwartz
Assistant Examiner—Philip W. Carter
Attorney, Agent, or Firm—Thomas D. Brainard

[57] ABSTRACT

In a first aspect, the invention involves a reactive support useful for automated synthesis of oligonucleotides. The reactive support comprises a label moiety (e.g. hapten) covalently bonded via a stable bond to a trifunctional spacer. The labeled trifunctional spacer complex is covalently bonded to a solid support via a cleavable bond. One arm of the trifunctional spacer attaches the solid phase; another arm attaches the label; while the third arm provides a hydroxyl group useful for synthesizing a labeled oligonucleotide. Upon synthesis, the cleavable bond is broken, yielding the labeled oligonucleotide. Methods for labeling oligonucleotides and useful kits are also described.

27 Claims, No Drawings

METHODS, KITS, AND REACTIVE SUPPORTS FOR 3' LABELING OF OLIGONUCLEOTIDES

This invention relates to the covalent coupling of detectable marker molecules into nucleic acid segments referred to as oligonucleotides. More specifically, it relates to a solid support and methods useful for automated 3' end labeling of oligonucleotides.

BACKGROUND

Labeled oligonucleotides find utility in a number of applications, including DNA sequencing, diagnostic detection or quantitation and forensic science. Typically, the labeled oligonucleotide is allowed to hybridize or anneal with nucleic acid present in the sample and the presence or absence of label is detected following separation steps.

Many mechanisms and schemes have been used to introduce labels into oligonucleotides. For a comprehensive review of these methods see Goodchild, *Bioconjugate Chemistry*, 1(3):165-187 (1990). According to Goodchild, past researchers have labeled oligonucleotides at both internal and terminal locations; by enzymatic and chemical synthetic means; and utilizing a single or many marker molecules per oligonucleotide. Methods involving incorporation of marker moieties at internal locations in the oligonucleotides are generally less preferable due to their less predictable hybridization behavior. For this reason, end labeled oligonucleotides are often preferred, particularly for automated detection systems. Similarly, methods for incorporating multiple label moieties into an oligonucleotide are less preferred for stoichiometric reasons. For some applications, it may not be critical that the labeled oligonucleotides are poorly characterized in terms of exact positioning and number of label molecules. However, for automated diagnostic detection, it is desireable that each oligonucleotide have a single marker moiety, preferably a haptenic "hook", at an end location.

Methods for placing a single marker, or hapten capable of reacting with an antibody or other specific binding member, at a terminal position on an oligonucleotide have been described in the literature. Most commonly, a linker member containing a primary amine or other nucleophilic group is attached at the 3' or 5' terminus to enable conjugation to one of numerous electrophilic detectable markers. Alternatively, terminal deoxynucleotidyl transferase, ligase and phosphoramidite chemistry have been used to attach direct labels or reactive linkers to oligonucleotides.

For example, Kempe, et al., *Nucleic Acids Research* 13(1):45-57 (1985) describe methods for post-synthesis biotinylation of 3' termini. A first method involves oxidation of the 3' hydroxyl to a 3' aldehyde, followed by condensation with alkyl diamines to provide a reactive amine for condensation with biotin. In a second method, biotin is attached to the 3' end by RNA ligase.

Zuckermann, et al., *Nucleic Acids Research* 15(13): 5305-5321 (1987) describe nucleosides modified to incorporate a linker arm having a disulfide link. The disulfide link is used to attach the modified nucleoside to a solid support. The nucleoside is then able to undergo oligonucleotide synthesis according to the phosphoramidite or phosphotriester methods. Following synthesis, the disulfide is cleaved and the free sulfhydryl group may be used to attach a fluorescent reporter to the probe.

Nelson, et al., *Nucleic Acids Research* 17(18): 7187-7194 (1989) describe a control pore glass solid support having incorporated therein a multifunctional agent having both a masked amino group and a protected hydroxyl group. The hydroxyl group can be used for standard synthesis of oligonucleotides as is known in the art. The protected amino group can be used after synthesis and cleavage of the oligonucleotide for coupling to a reporter molecule. This approach is very much like the commercially available 3' Amine-On CPG TM (Clontech, Palo Alto, Calif.)

Each of the above methods have been used successfully to incorporate detectable marker compounds into 3' end positions of oligonucleotides. However, none is readily adaptable to automated synthesis such that the label moiety can be added to the oligonucleotide prior to cleavage from the support. In each case, the oligonucleotide must undergo one or more additional steps to couple the label to the cleaved oligonucleotide. This is undesirable if commercial quantities of labeled oligonucleotides are to be produced by automated synthesis.

Accordingly, the present invention seeks to overcome the problems associated with prior methods, and to provide a solid support and a method for 3' end labeling of oligonucleotides which is amenable to automated chemical synthesis. A method for preparing such a novel support is also described.

SUMMARY OF THE INVENTION

In a first aspect, the invention is a reactive support useful for automated synthesis of oligonucleotides. The reactive support comprises a label moiety covalently bonded via a stable bond to a trifunctional spacer containing the hydroxyl group to form a labeled spacer complex, and the labeled trifunctional spacer complex is covalently bonded to a solid support via a cleavable bond. The trifunctional spacer which connects the label moiety, the hydroxyl and the solid phase may be cyclic, heterocyclic or chain-like as described below. Preferably, the spacer will be chain-like and the reactive support will have the general formula:

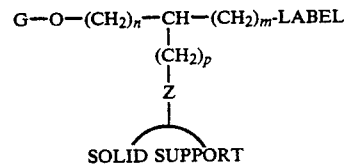

wherein n and m independently are integers from 1 to about 30; p is an integer from 0 to about 30; G is H or a protecting group; and Z is a linking group having a cleavable bond.

Preferably, n and m independently are integers from 1 to about 8, more preferably 1 to 3; and p is an integer from 0 to about 8, more preferably, zero to 3, ideally zero. The cleavable linkage preferably includes an acid stable, base labile cleavable bond, such as an ester bond. This permits use of the reactive support with known automated synthesizer protocols.

In another aspect, the invention includes a process of preparing a reactive support having a label and a hydroxyl group useful for synthesizing a labeled oligonucleotide. The process includes the steps of:
a. providing a trifunctional linker with three functionalities, a first one of whose functionalities is a hydroxyl group or a protected hydroxyl group and each of whose functionalities has or can be made to have a differential reactivity;

b. reacting the second functionality of said trifunctional linker with a label moiety having a reactive group capable of reacting with the second functionality to form a stable bond connecting the label moiety to the trifunctional linker; and c. reacting the third functionality of the trifunctional linker with one or more reagents capable of imparting a cleavable bond to the trifunctional linker, and with a functionalized solid support under conditions such that the trifunctional linker is covalently attached to the solid support via the cleavable bond.

The trifunctional linker, like the trifunctional spacer which it becomes, may be cyclic, heterocyclic or chain-like. Preferably, the trifunctional linker is chain-like and has the general formula:

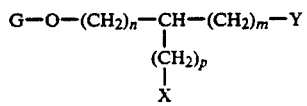

wherein n and m independently are integers from 1 to about 30; p is an integer from 0 to about 30; G is H or a protecting group; and X and Y are independently selected from the group consisting of hydroxyl, amino, thiol and carboxyl. Preferably, n and m independently are integers from 1 to about 8, more preferably 1 to 3; and p is an integer from 0 to about 8, more preferably, zero to 3, ideally zero. It should be recognized that the trifunctional spacer is the trifunctional linker minus its reactive functionalities X and Y.

In yet another aspect of the invention, a method for labeling the 3' end of an oligonucleotide synthesized on a solid support is described. The method includes preparing a reactive support having a protected hydroxyl group according to the above method, followed by deprotecting the hydroxyl group and synthesizing an oligonucleotide from the deprotected hydroxyl group. Preferably, the oligonucleotide is synthesized by known, automated methods.

Finally, the invention encompasses a kit comprising the reactive support described above wherein the label comprises a hapten; and an antihapten antibody conjugated to a detectable marker or to a solid phase. Preferably, the detectable marker is an enzyme label. Optionally, the kit may include protected nucleic acid phosphoramidite reagents necessary for DNA synthesis.

DETAILED DESCRIPTION

Reactive Support

The novel reactive support of the present invention can be generally characterized by the formula:

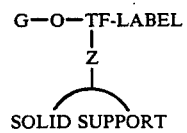

wherein Z represents a linking group having a cleavable bond; TF represents a trifunctional spacer as described below; G is H or a protecting group; and LABEL represents the detectable label moiety, preferably a hapten.

More preferably, the reactive support comprises the following general structure:

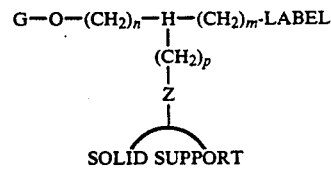

wherein n and m independently are integers from one to about 30; p is an integer from 0 to about 30; G is H or a protecting group; and Z is a linking group having a cleavable bond. Preferably, integers m and n are between 1 and about 8, and p is between 0 and about 8. Most preferably, n and m are from 1 to 3 and p is from 0 to 2, often 0.

A central feature of the novel reactive support is a trifunctional spacer deriving from a trifunctional linker molecule. A trifunctional linker is a reagent having three reactive functionalities, wherein a first one of the functionalities is a protected hydroxyl group and each of the three functionalities has or can be made to have a differential reactivity. The term "trifunctional spacer" is used when two of the reactive functionalities of the linker have been reacted with other molecules, leaving only the protected hydroxyl group (which is used for synthesis of an oligonucleotide).

The trifunctional reagent (linker or spacer, collectively designated "TF") may comprise a number of different configurations, provided it meets the definition above. For example, the TF may be cyclic, having the general formula:

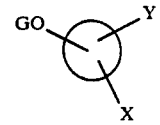

Substituent —OG is the first reactive functional group, while X and Y represent the remaining two reactive functionalities. The ring structure may be 5-7 atoms, preferably carbons. The single link shown connecting —OG, X and Y to the ring may be a single bond, or it may represent two or more bonds, for example in an alkyl chain. Where any two of the reactive functionalities are the same, it is preferred that the bond connecting one differs from the bond connecting the other. In this manner, the two same functionalities can have differential reactivities. For example, if Y is a hydroxyl group, (as is OG) it is preferably to join one directly to the ring, making it a secondary alcohol, while the other is spaced by at least one methylene group, thereby making it a primary alcohol. An exemplary TF of this type is shown below.

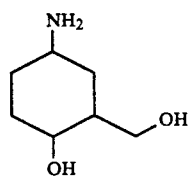

Alternatively, the TF may be heterocyclic as shown in the general formula:

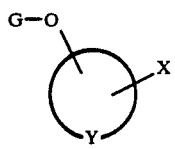

Substituent —OG is the first reactive functional group; X and Y represent the remaining two reactive functionalities. N is the most desirable functionality for Y in this configuration, due to its trivalent nature. The ring may again comprises from 5-7 atoms, preferably carbon. Once again, if X is hydroxyl it is preferred to achieve differential reactivity by making G or X a secondary group while the other is made primary. Exemplary TFs of this type are shown below.

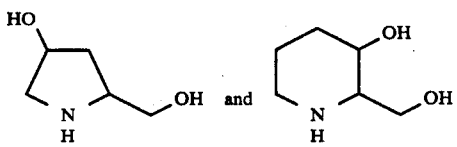

A preferred TF is chain-like and has the general formula:

$$G-O-(CH_2)_n-CH-(CH_2)_m-Y$$
$$\underset{X}{\underset{|}{(CH_2)_p}}$$

wherein integers n, m and p, and substituent G are as previously defined. Substituent —OG is the first reactive functional group; X and Y represent the remaining two reactive functionalities. As will be described below, the trifunctional linker is useful in preparing the novel reactive support. The preferred linker (as well as the corresponding spacer of the reactive support) contains three spacer arms, one between each reactive functionality and the central carbon atom. The length of these spacer arms is controlled by the integers n, m and p. A smaller number for n and m permits a more compact link of the label moiety to the hydroxyl from which DNA is synthesized. The smaller p is, the smaller is the tail or residue which remains attached to the labeled, synthesized DNA upon completion. This is because p controls the length of the spacer between the cleavable bond and the remainder of the bifunctional linker.

In addition, the nature of the spacer arms in the trifunctional linker is not deemed critical, it is contemplated that other spacer groups are equivalents. For example, it may be possible to substitute at least some of the methylene spacers with other groups without loss of equivalence. For example, ether linkages, branched alkyl linkages and aromatic linkages may be utilized, provided they form relatively stable bonds and that the groups do not interfere with DNA synthesis, hybridization or label detection.

The solid support preferably comprises controlled pore glass (CPG). CPG is commercially available from a number of sources including CPG, Inc. Fairfield, N.J. As an alternative, various resins may be suitable as solid supports, including polystyrene (e.g. TentaGel TM resin, available from Rapp Polymere, Tübingen, Germany). For simplified preparation (see below), the solid support should be derivatized so as to contain a reactive group to which the trifunctional linker may be bonded via a cleavable bond. Various reactive groups may serve as the derivative such as hydroxyl, amino, thiol and carboxyl, although hydroxyl and amino are preferred.

Label moieties useful in the invention may comprise a wide variety of compounds. At least three types of label moieties can be used with the invention:

1. A direct label which is capable of being detected directly, such as a radioactive or chemiluminescent marker;
2. A modulated label moiety, which requires the addition of an external stimulus in order to be detected, such as fluorescent labels (requiring the stimulus of incident radiation); and
3. "Hook" type label moieties which generally comprise haptens capable of being recognized by a specific binding member which ultimately bears one of the first two types of labels or an enzyme label.

In the present invention, haptens are the preferred label moieties. These can be detected by specific binding partners such as antibodies which have been coupled to detectable markers such as enzymes. Exemplary haptens include biotin, fluorescein, dansyl and many others. Virtually any compound which can be made to elicit an immune response to form antibodies can be used as a hapten in the present invention, provided it is stable to the relatively harsh conditions of nucleic acid synthesis. These conditions have been described in detail in the literature, but briefly comprise an acidic detritylation step, an oxidation step, and a basic base deprotection step.

Preferably, a protecting group prevents the first functionality from reacting in undersirable situations. This procedure is well known to those of skill in this art to preserve a hydroxyl group for subsequent synthesis of DNA or other oligonucleotides. Suitable protecting groups include dimethoxytrityl (DMT), monomethoxytrityl (MMT), tetrahydropyranyl (THP) and substituted THP, 2 methoxyethoxymethyl (MEM) and substituted ethyl ethers such as t-butyl ether and 1-ethoxyethyl ether.

The final component of this solid support is a linking group, Z, containing a cleavable bond. By "cleavable bond" is meant a bond which is stable to, and not cleaved by, conditions under which automated DNA or RNA synthesis occurs, including conventional detritylation steps under acidic conditions, but which can be broken under other conditions. Accordingly, it is preferred that the cleavable bond is a bond which is acid stable and base labile, such as an ester. Upon complete synthesis of the desired DNA or RNA molecule, the cleavable bond serves to separate the synthesized molecule from the solid support. It is therefore preferable that the cleavable bond occur within the linking group Z in close proximity to the remainder of the trifunctional linker molecule so that little or no residue is left thereon which might interfere with DNA hybridization. Typical examples of cleavable bonds include esters, disulfides and viccinal diols (e.g. from tartrate).

In contrast, a "stable bond" is one which will withstand both the conditions of automated DNA or RNA synthesis and the conditions under which the synthesized oligonucleotide is severed from the solid support. A stable bond will also withstand the conditions of hybridization, and preferably the conditions of amplification. Stable bonds include C—C bonds, C—N bonds and many similar bonds between a carbon atom and a heteroatom, (e.g. amide bonds).

As will be discussed below, a preferred cleavable bond is an ester linkage introduced through the reaction of a secondary hydroxyl functionality on the trifunctional linker with an acid anhydride. The acid function may then be reacted (following activation if necessary) with the derivatized solid support. Thus, the resulting linking group Z contains two components: a cleavable ester bond adjacent the trifunctional linker, and a spacer arm between the cleavable bond and the solid support. The spacer arm may include any length of spacer positioned between the solid and the derivatized reactive group. This space can be virtually any length from about 2 to about 40 or more atoms. The nature of these spacer molecules is not critical provided the bonds therein are capable of remaining intact during conventional DNA synthesis. Both short and long chain alkyl amino glass supports have been used, and are commercially available (CPG, Inc.). No optimal spacer length has been determined, which suggests that this is not a critical element of the invention.

METHODS

A process of preparing the novel solid phase has been suggested above, and relies on the trifunctional linker. A trifunctional linker is a relatively small molecule having three reactive functionalities which are or can be made to have differential reactivity. The trifunctional linker reagents and the corresponding spacers (TF) are discussed above. In the preferred chain-like TF, each of the functionalities resides on a short spacer arm extending from a central carbon. A general formula was set forth above.

As stated above, the length of the spacer groups designated by the methylene groups repeated n, m or p times within the structure depends on the integers n, m and p, which are preferably small. Integer p may also be zero, whereby the reactive functionality X constitutes a secondary group (e.g. secondary alcohol or amino). This is a preferred method for achieving differential reactivity between this functionality and an identical reactive group in a primary position. For example, diols and triols may be used when one hydroxyl is secondary. As stated previously, substituents for the methylene groups are deemed equivalent as spacers, provided the bonds are stable.

At least a first one of the reactive functionalities is a hydroxyl or a protected hydroxyl group which ultimately serves as the basis for automated DNA synthesis. Generally, the remaining reactive functionalities will include hydroxyl, amino, and/or carboxyl groups. Each of the three reactive functionalities may be the same or different provided they have, or can be made to have, differential reactivity. By way of example, the remaining two reactive functionalities may have the configuration shown in the table below.

TABLE I

| SECOND GROUP, Y (primary) | THIRD GROUP, X (secondary) | Note |
| --- | --- | --- |
| —OH | —OH | provided the first hydroxyl (primary OG) is protected, or otherwise differentiable from the second primary alcohol, Y |
| —OH | —NH$_2$ | provided the first hydroxyl (primary OG) is protected, or otherwise differentiable from the second primary alcohol, Y |
| —OH | —COOH | provided the first hydroxyl (primary OG) is protected, or otherwise differentiable from the second primary alcohol, Y |
| —NH$_2$ | —OH | |
| —NH$_2$ | —NH$_2$ | |
| —NH$_2$ | —SH | |
| —NH$_2$ | —COOH | |
| —SH | —OH | |
| —SH | —NH$_2$ | |
| —SH | —COOH | |

One of the remaining two reactive functionalities is used to covalently bond the label moiety via a stable bond. The chemistry of linking a label moiety via a stable bond is conventional. Many reactants are known to one of skill in the art for coupling the various reactive functionalities with available groups on the label. For example, amino functionalities can be made to react with sulfonyl chlorides, carboxyls (after activation or via carbodiimide), hydroxyls (after tosylation) and thiols (via maleimide). Similarly, hydroxyl functionalities can be made to react with anhydrides and amines. Many other examples could be given.

The other remaining functionality (generally the secondary functionality) may be used to introduce at least part of the cleavable linking group, Z, which contains the cleavable bond. As suggested above, a preferred method for introducing a cleavable bond involves reacting the third functionality with a cleavable linking group. The linking group contains a cleavable bond and generates another reactive group for bonding to the solid support. Specifically, reacting a secondary hydroxyl functionality with a cyclic acid anhydride yields an ester with a carboxyl reactive group. The ester bond so formed is a cleavable bond as defined herein. The carboxylic acid may be converted to an active ester which will react with an amino derivatized solid support. The carboxyl group may be otherwise modified to react with other derivative groups on the solid support.

Exemplary acid anhydrides include succinic and maleic anhydride, though others are deemed equivalent. In addition, other methods of introducing a cleavable bond between the trifunctional linker and the solid support are deemed within the scope of the invention.

The order of reacting the reactive functionalities is not critical to the invention. It is important however that the bonds formed in an earlier step can withstand the conditions necessary to create the bonds of a subsequent step. Thus, it will be recognized by those of skill in the art that the label may generally be attached first since it is desired that this be a more stable bond. The linking group including its cleavable bond, is generally added next. Of course, the final functionality will remain a protected hydroxyl group and is used for subsequent synthesis of a nucleic acid to which the label will be attached at a 3' end.

It will be understood by those of ordinary skill in this art, that intermediate protecting and deprotecting steps may be required although they have not been set forth in detail herein. Protecting groups may be required to achieve the differential reactivity required of the invention. For example, a triol trifunctional linker (e.g. two primary hydroxyls and one secondary) is possible if one can differentiate the two primary hydroxyls. Example 1 shows one method of achieving this. Conventional protecting groups such as DMT or MMT may also be required to preserve the hydroxyl group necessary for oligonucleotide synthesis.

Having prepared the novel solid phase, a method of using it to label an oligonucleotide is described. Automated DNA synthesizers, such as the Applied Biosystems 380B, are commercially available. Use of such an automated synthesizer is preferred in this invention. The labeled solid support is added to the instrument along with the requisite nucleic acid phosphoramidite reagents. If the support contains a protecting group on the hydroxyl, as is preferred, the first step will be the removal of the protecting group. Using the available hydroxyl, DNA is synthesized according to the manufacturer's instructions. Upon completion of synthesis, the support is exposed to conditions which break the cleavable bond, thus separating the synthesized DNA from the solid support. Typically, basic conditions are employed.

The synthesized DNA can be used as probes for the detection of complementary DNA in a sample. It may also be used as probes in an amplification scheme known as ligase chain reaction (LCR) if the appropriate probes are labeled at the 3' end. LCR is described in EP-A-320 308 and elsewhere in the literature.

KITS

The invention also contemplates kits comprising 1) the reactive support of the invention wherein the label comprises a hapten; and 2) an antihapten antibody. In most cases, the antibody is conjugated to a detectable marker. The kits can then be employed to synthesize DNA or RNA which is labeled at its 3' end with a hapten. The antibody may be used to detect the DNA or RNA if conjugated to a detectable marker, such as an enzyme.

Alternatively, the antibody conjugate may be used for separation of the DNA or RNA from other sample components. This conjugate requires an antihapten antibody coated or immobilized on an insoluble solid phase. This "capture" antibody may be used to separate haptenated oligonucleotides from unlabeled oligonucleotides and other sample components. This aspect is particularly useful in LCR where template dependent ligation couples another (labeled) probe to the haptenated probe only in the presence of target. The capture antibody conjugate can effect separation, while the label on the other (ligated) probe can be determined as a measure of sample DNA or RNA.

Optionally, the kits may contain the deoxyribonucleoside or ribonucleoside phosphoramidite reagents necessary for DNA or RNA synthesis.

EXAMPLES

EXAMPLE 1

Synthesis of Dansyl-CPG using an Aminopropanediol Linker

A. Dansyl-diol

A hapten, dansyl chloride (1.0 gram, 3.7 mmol) was dissolved in THF(20 mL) and added dropwise to a cooled solution of the trifunctional linker, 3-amino-1,2-propanediol (0.34 gram, 3.7 mmol) in 10% sodium carbonate (20 mL). After the addition, the ice bath was removed and the reaction stirred at room temperature, protected from light, for 18 h. The reaction utilizes the amino functionality to give a labeled diol product, which was extracted with ethyl acetate, dried and the solvent removed under reduced pressure. The yield was 1.1 grams of product, pure enough for the next reaction.

B. Dansyl-diol-DMT

Dansyl-diol (1.1 grams, 3.4 mmol) was dissolved in pyridine (20 mL) and then diisopropylethylamine (0.9 mL, 51 mmol), N,N-dimethylaminopyridine (0.02 grams, 0.17 mmol), and 4,4'-dimethoxytritylchloride (1.3 grams, 37 mmol) were added. The reaction was stirred at room temperature for 18 h then the solvent was removed under reduced pressure. The product (labeled trifunctional linker having a protected primary hydroxyl) was purified by flash chromatography, eluting with 2:8, ethyl acetate/hexanes. The solvent was removed giving a yellow glass weighing 1.4 grams.

C. Dansyl-diol-DMT-succinic acid ester

Dansyl-diol-DMT (1.0 gram, 1.6 mmol) was dissolved in pyridine (7 mL). To this solution was added succinic anhydride (0.17 gram, 1.7 mmol), diisopropylethylamine (0.042 mL, 2.4 mmol), and N,N-dimethylaminopyridine (0.01 gram, 0.08 mmol). The reaction was stirred at room temperature, under nitrogen atmosphere, for 18 h. The solvent was removed under reduced pressure and the residue was purified by flash chromatography using silica gel (200-400 mesh), eluting with 5:95, methanol/dichloromethane. The yield was 0.97 gram of the ester, which introduces a cleavable bond.

D. Dansyl CPG

Dansyl-diol-DMT-succinic acid ester (0.3 gram, 0.44 mmol) was dissolved in N-methylpyrrolidinone (NMP) (3 mL). To this solution was added N-hydroxysuccinimide (0.061 gram, 0.53 mmol), and N,N'-dicyclohexylcarbodiimide (0.1 gram, 0.48 mmol). The reaction was stirred at room temperature, under nitrogen atmosphere, for 8 h. The reaction was filtered and the filtrate added to 0.5 grams of controlled pore glass (CPG Inc., LCA00500C, lot 06C406). Enough NMP was added to allow the CPG to mix while being agitated on a rotator, and diisopropylethylamine (0.3 mL, 1.8 mmol) was then added. After 48 h, the glass was washed with acetonitrile, dichloromethane and then dried under reduced pressure, giving the labeled solid support.

EXAMPLE 2

Synthesis of Dansyl-CPG Using an Aminohexanediol Linker

Example 1 is repeated except that 6-amino-1,3-hexanediol is used in place of the 3-amino-1,2-propanediol as the trifunctional linker.

EXAMPLE 3

Synthesis of Dansyl-Polystyrene Support

Dansyl-4,6-diol-DMT-TentaGel

Dansyl-diol-DMT-succinic acid ester (0.265 gram, 0.34 mmol), as prepared in Example 1 above, was combined with p-nitrophenol (0.05 gram, 0.36 mmol) and N,N'-dicyclohexycarbodiimide (0.78 gram, 0.38 mmol) in tetrahydrofuran (3 mL). The reaction was stirred at room temperature for 4.5 hours then filtered to remove the precipitated N,N'-dicyclohexylurea. The solution was added to TentaGel resin Amine NH$_2$ (0.5 gram, 0.23 meq NH$_2$/gram, RAPP POLYMERE, Tübingen) along with dry acetonitrile (2 mL) and the reaction agitated using a rotator. After 48 hours, the resin was isolated, washed with acetonitrile, then with methylene chloride, and dried first with a nitrogen stream then with reduced pressure.

What is claimed is:

1. A reactive support having a free or protected hydroxyl group useful for synthesis of an oligonucleotide, said support comprising a label moiety covalently bonded via a stable bond to a trifunctional spacer containing the hydroxyl group to form a labeled linker complex, the labeled linker complex being covalently bonded to a solid support via a cleavable bond.

2. The reactive support of claim 1, further having the formula:

$$\text{G—O—(CH}_2)_n\text{—CH—(CH}_2)_m\text{-LABEL}$$
$$|$$
$$\text{(CH}_2)_p$$
$$|$$
$$\text{Z}$$
$$|$$
$$\text{SOLID SUPPORT}$$

wherein n and m independently are integers from 1 to about 30; p is an integer from 0 to about 30; G is H or a protecting group; and Z is a linking group having a cleavable bond.

3. The reactive support of claim 2 wherein n and m independently are integers from 1 to about 8, and p is an integer from 0 to about 8.

4. The reactive support of claim 3 wherein n and m independently are integers from 1 to 3, and p is an integer from 0 to 3.

5. The reactive support of claim 2 wherein Z includes an acid stable, base labile cleavable bond.

6. The reactive support of claim 5 wherein Z includes a cleavable bond comprising an ester linkage.

7. The reactive support of claim 1 wherein the solid support is selected from the group consisting of controlled pore glass and polymeric resins.

8. The reactive support of claim 1 wherein the label moiety is a hapten.

9. The reactive support of claim 1 wherein the trifunctional spacer is a cyclic or heterocyclic molecule.

10. A reactive support having a free or protected hydroxyl group useful for synthesis of an oligonucleotide, said support comprising a label moiety covalently bonded via a stable bond to a trifunctional spacer containing the hydroxyl group to form a labeled linker complex, the labeled linker complex being covalently bonded to a solid support via a cleavable bond; wherein said trifunctional spacer is a cyclic or heterocyclic molecule.

11. A process of preparing a reactive support having a label and a hydroxyl group useful for synthesizing a labeled oligonucleotide, said process comprising:

a. reacting the second functionality of a trifunctional linker having three functionalities, a first one of whose functionalities is a hydroxyl group or a protected hydroxyl group and each of whose functionalities has or can be made to have a differential reactivity, with a label moiety having a reactive group capable of reacting with the second functionality to form a stable bond connecting the label moiety to the trifunctional linker; and b. reacting the third functionality of the trifunctional linker with one or more reagents capable of imparting a cleavable bond to the trifunctional linker, and with a functionalized solid support under conditions such that the trifunctional linker is covalently attached to the solid support via the cleavable bond.

12. The process of claim 11 wherein the second and third reactive functionalities of the trifunctional linker are independently selected from the group consisting of hydroxyl, amino, and thiol.

13. The process of claim 11 wherein the reagent of step b capable of imparting a cleavable bond to the trifunctional linker is selected from the group consisting of succinic anhydride and maleic anhydride to impart a cleavable ester.

14. The process of claim 11 wherein the reagent of step b capable of imparting a cleavable bond to the trifunctional linker imparts an acid stable, base labile bond.

15. The process of claim 11 wherein the label moiety comprises a hapten.

16. The process of claim 11 wherein said trifunctional linker has the formula:

$$\text{G—O—(CH}_2)_n\text{—CH—(CH}_2)_m\text{—Y}$$
$$|$$
$$\text{(CH}_2)_p$$
$$|$$
$$\text{X}$$

wherein n and m independently are integers from 1 to about 30; p is an integer from 0 to about 30; G is H or a protecting group; and X and Y are independently selected from the group consisting of hydroxyl, amino, thiol and carboxyl.

17. The process of claim 16 wherein n and m independently are integers from 1 to about 8, and p is an integer from 0 to about 8.

18. The process of claim 17 wherein n and m independently are integers from 1 to 3, and p is an integer from 0 to 3.

19. A reactive support prepared by the process of claim 11.

20. A method for labeling the 3' end of an oligonucleotide synthesized on a solid support, said method comprising:

a. reacting the second functionality of a trifunctional linker having three functionalities, a first one of whose functionalities is a protected hydroxyl group and each of whose functionalities has or can be made to have a differential reactivity, with a label moiety having a reactive group capable of reacting with the second functionality to form a stable bond connecting the label moiety to the trifunctional linker;

b. reacting the third functionality of the trifunctional linker with one or more reagents capable of imparting a cleavable bond to the trifunctional linker, and with a functionalized solid support under conditions such that the trifunctional linker is covalently attached to the solid support via the cleavable bond.

c. deprotecting the hydroxyl group; and d. synthesizing an oligonucleotide from the deprotected hydroxyl group.

21. The method of claim 20 comprising a further step of cleaving the synthesized oligonucleotide from the support at the cleavable bond.

22. The method of claim 20 wherein the second and third reactive functionalities of the trifunctional linker are independently selected from the group consisting of hydroxyl, amino, thiol and carboxyl.

23. The method of claim 20 wherein the reagent of step b capable of imparting a cleavable bond to the trifunctional labeled product is selected from the group consisting of succinic anhydride and maleic anhydride.

24. The method of claim 20 wherein the label moiety comprises a hapten.

25. A kit comprising:
 a. the reactive support of claim 1, wherein the label comprises a hapten; and
 b. an antihapten antibody conjugated to a detectable marker or to a solid phase.

26. The kit of claim 25 wherein the detectable marker is an enzyme label.

27. The kit of claim 25, further comprising in separate containers deoxyribonucleoside triphosphates or ribonucleoside triphosphates.

* * * * *